(12) United States Patent
Qasem

(10) Patent No.: US 10,792,388 B1
(45) Date of Patent: Oct. 6, 2020

(54) DEVELOPED SAFETY PORTABLE INCENSE HEATER

(71) Applicant: Sadeq Ahmad Qasem, Adan (KW)

(72) Inventor: Sadeq Ahmad Qasem, Adan (KW)

( * ) Notice: Subject to any disclaimer, the term of this patent is extended or adjusted under 35 U.S.C. 154(b) by 11 days.

(21) Appl. No.: 16/367,261

(22) Filed: Mar. 28, 2019

(51) Int. Cl.
*A61L 9/03* (2006.01)

(52) U.S. Cl.
CPC .................................... *A61L 9/032* (2013.01)

(58) Field of Classification Search
CPC ....................................................... A61L 9/032
USPC ........................................................... 422/124
See application file for complete search history.

(56) References Cited

U.S. PATENT DOCUMENTS 9,974,119 B1    5/2018  Qasem

*Primary Examiner* — Lessanework Seifu

(57) ABSTRACT

The present invention relates generally developed safety portable incense heater and more particularly to a self-contained incense heater shaped a reversed (L) letter for safely holding, igniting and heating incense (bukhoor wood bricks). The developed safety portable incense heater shaped a reversed (L) letter is going to heat the incense (bukhoor wood bricks) with a certain temperature in order to help the user to direct the smoke flow in the exact direction of the nozzle using the fan thrust. The self-contained developed safety incense heater shaped a reversed (L) letter has a small as pocket size and is portable without any wires to enhance the mobility of the users and the way of using incense or bukhoor wood bricks.

11 Claims, 6 Drawing Sheets

DEVELOPED SAFETY PORTABLE INCENSE HEATER

BACKGROUND OF THE INVENTION

1. Field of the Invention

The present invention relates generally portable incense heater and more particularly to a self-contained incense heater shaped a reversed (L) letter for safely holding, igniting and heating the incense or and the bukhoor wood bricks.

2. Description of the Related Art

Incense burners or heaters are well known and have been in use for many years. Burners or heaters of various designs are appropriate for different applications ranging from religious services to a device for killing flying insects and/or dispensing a pleasant aroma.

For example, a U.S. Pat. No. 9,974,119 of SADEQ relates to self-contained incense burner shaped a hairdryer for safely holding, igniting and burning incense. The portable incense burner shaped a hairdryer is going to heat the incense with a certain temperature in order to help the user to direct the smoke flow in the exact direction of the nozzle using the fan thrust. The self-contained incense burner shaped a hairdryer has a small as pocket size and is portable without any wires to enhance the mobility of the users and the way of using incense.

There are some disadvantages for incense burner in the U.S. Pat. No. 9,974,119 as (1) heat up time of the old heating cartridge (a 3D print cartridge) was too slow (>30 seconds), (2) the heating performance of the old design was not efficient because of the following reasons: the heating cartridge was placed relative far from the incense (bukhoor) location (outside the incense (bukhoor) tray, and the heater body around the heating cartridge and metal part radiate heat in all directions without concentrating the heat on the incense (bukhoor), (3) the heating cartridge is placed close to the PCB which creates a risk of damaging the PCB by heat, (4) the incense (bukhoor) could move around ion the metal part and thereby reduce the heating efficiency a lot, and (5) the metal part and heating cartridge were not well insulated which cerate the risk of damaging casing parts by heat.

Notwithstanding the above it is presently believed that there is a potential demand and a commercial market for an incense heater and storage device in accordance with the present invention.

SUMMARY OF THE INVENTION

The present invention relates generally developed safety portable incense heater and more particularly to a self-contained incense heater shaped a reversed (L) letter for safely holding, igniting and heating incense or and the bukhoor wood bricks.

The developed safety portable incense heater shaped a reversed (L) letter is going to heat the incense or bukhoor wood inside it with a certain temperature in order to help the user to direct the smoke flow in the exact direction of the nozzle using the fan thrust. The self-contained incense heater shaped a reversed (L) letter is a small as pocket size and is portable without any wires to enhance the mobility of the users and the way of using incense or bukhoor wood bricks.

When the device is operated it sprays the fragrance, the incense of wood heating (bukhoor) and the user can use it or apply the fragrant mist on his body, cloths, hair and house or even any place.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
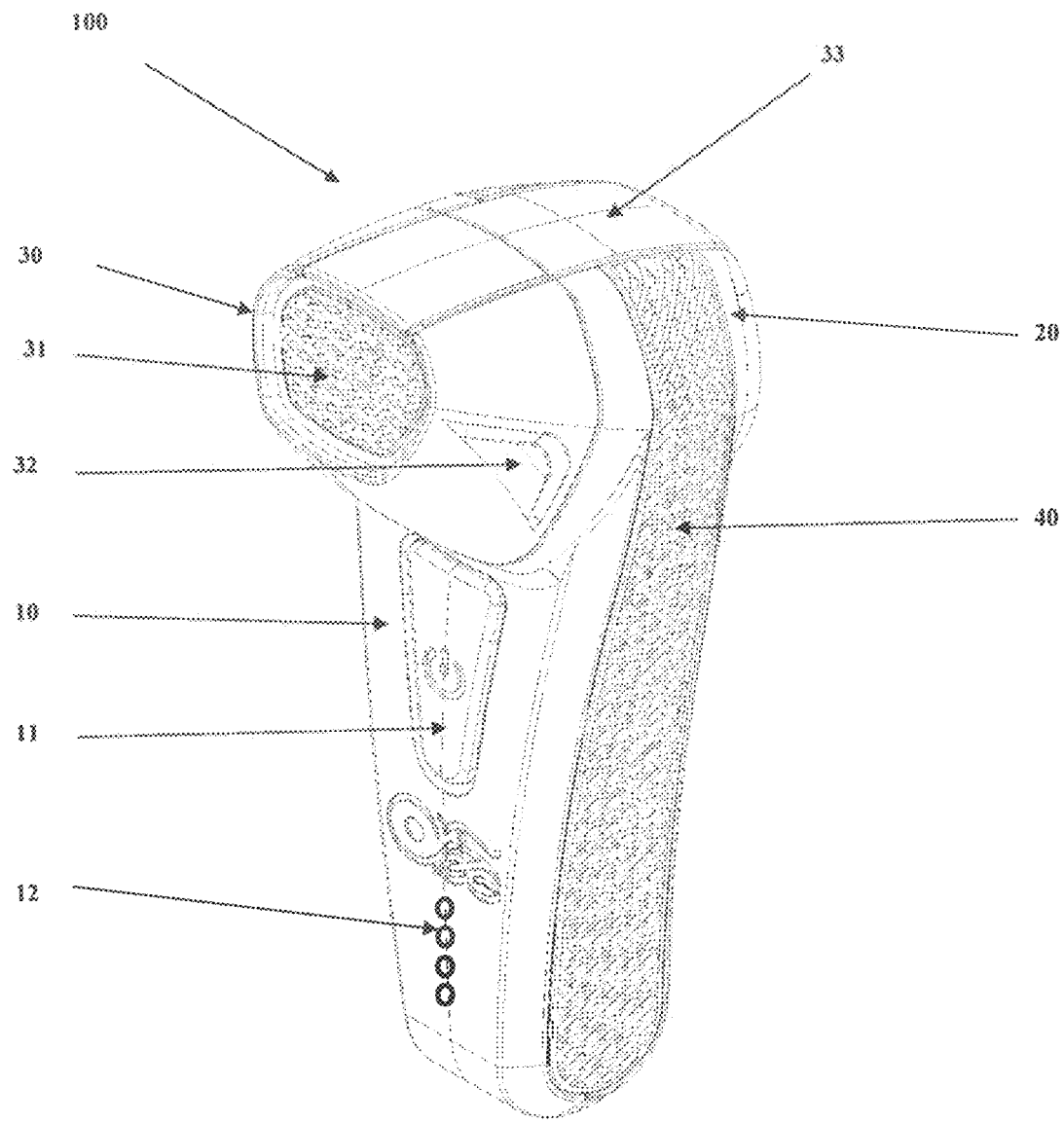
FIG. 1 is an outside perspective view of the developed safety portable incense heater showing outlet cap closed.
Figure 2:
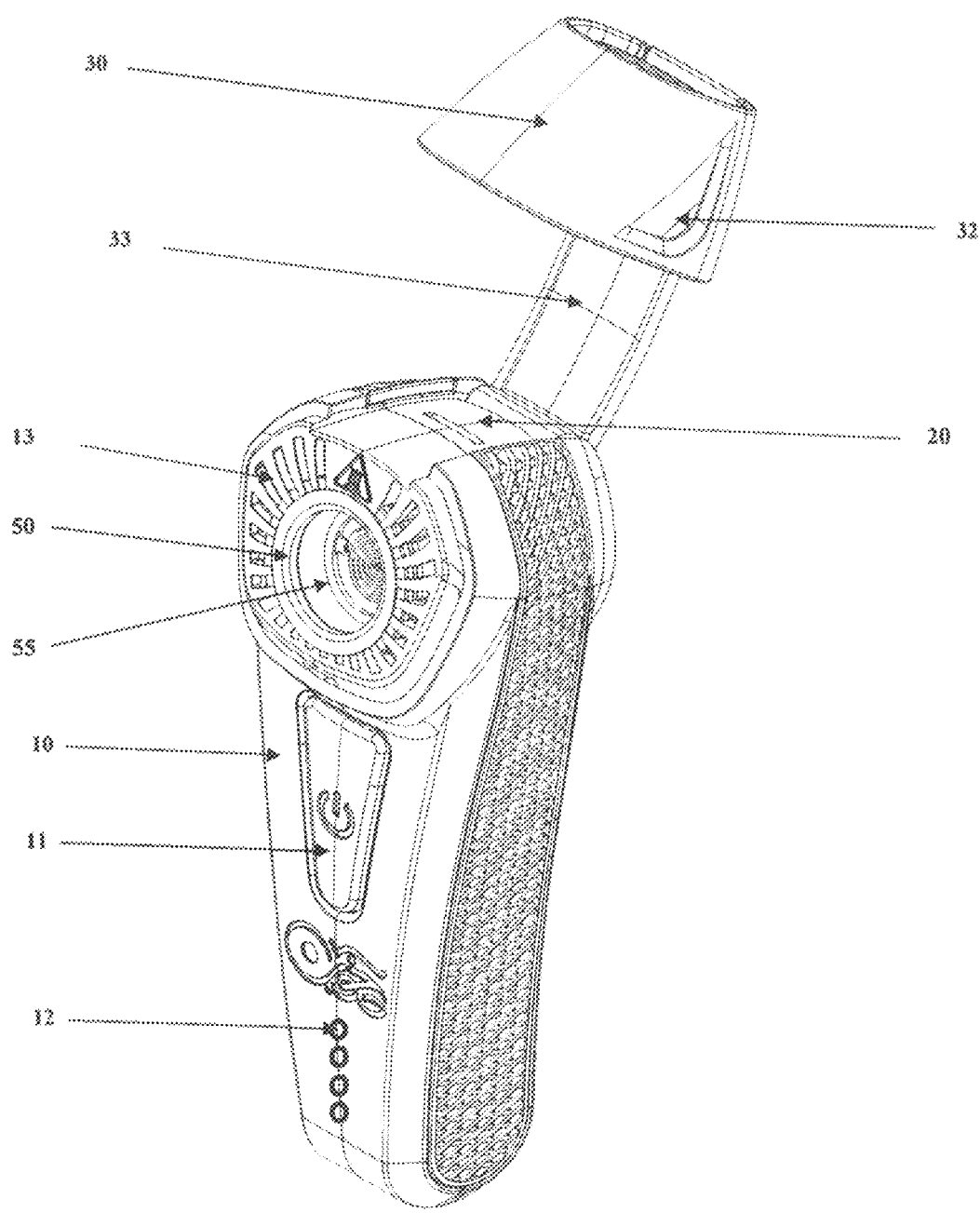
FIG. 2 is a perspective view of the developed safety portable incense heater showing outlet cap is opened.
Figure 3:
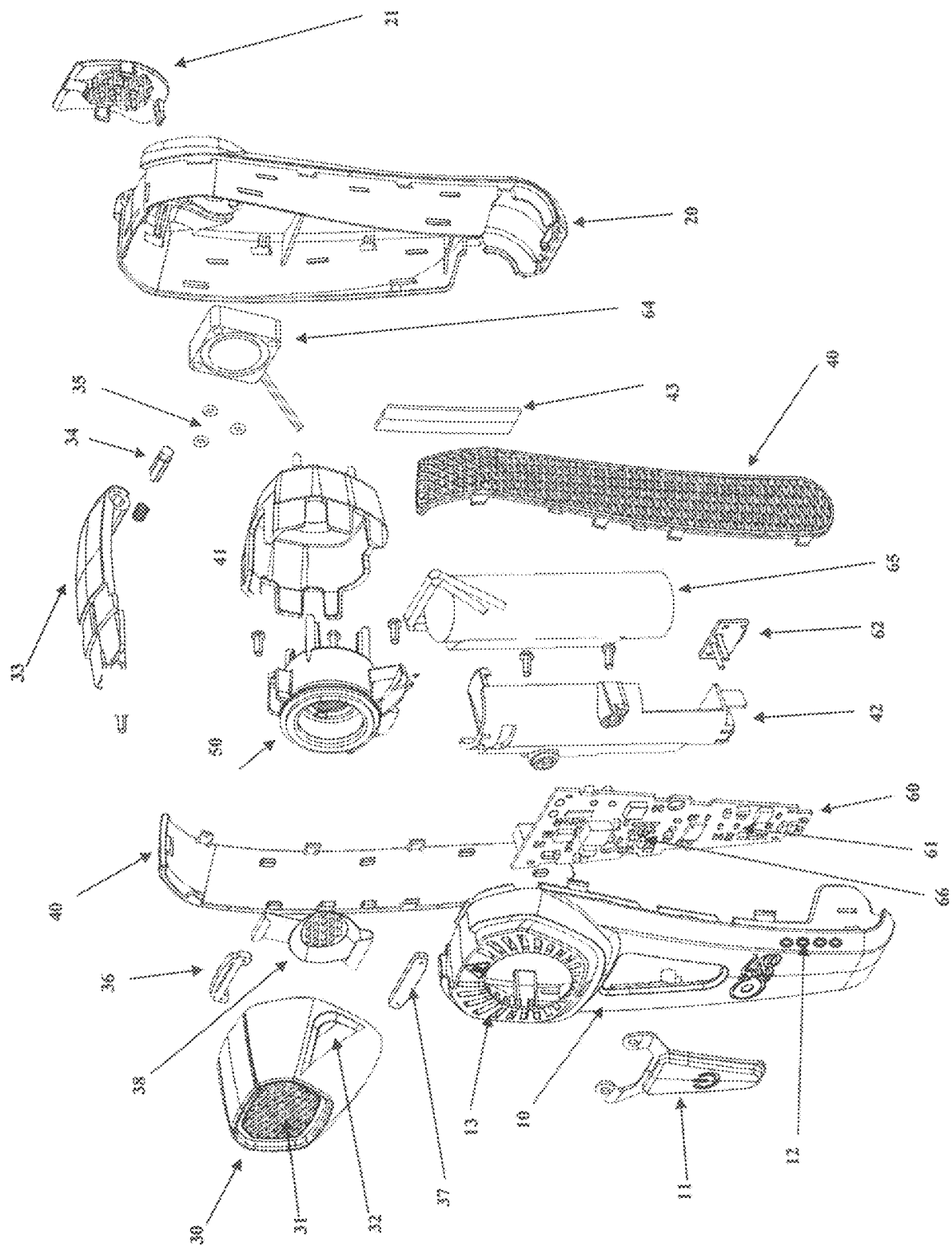
FIG. 3 is a detailed part exploded view of developed safety portable incense heater.

Referring to FIGS. 1, 2 and 3 which describe an outside perspective view of the developed safety portable incense heater 100 with cap closed, opened and detailed parts. The developed safety portable incense heater 100 comprises of a hollow housing body having a horizontal housing attached to a vertical housing shaped like reversed (L) letter, having a front housing 10 attached to rear housing 20. The front housing 10 which has a bottom curved end to mounted with the rear housing 20 and there are a right and left grill housing 40 attaching the two front and rear housing 10 and 20. On the top of front and rear housing 10 and 20 there is a hinge arm 33 which connected to the outlet cap 30 forming the like reversed (L) letter shape of the developed safety portable incense heater, hinge spring 34 mounted inside the hinge arm 33 to hold the outlet cap 30 and the hinge arm 33 while the users opens the present invention, the outlet cap 30 comprises of outlet grill 31, also right and left curved grooves 32 which helps the users for easily opening the outlet cap 30.

The front housing 10 comprises of main switch 11 and LED indication surface 12, both connected from behind front housing 10 to electronic PCB 60, the four LED 61 located exactly behind LED indication surface 12 on the front housing 10 so the users can see the status of the developed safety incense heater.

Figure 7:
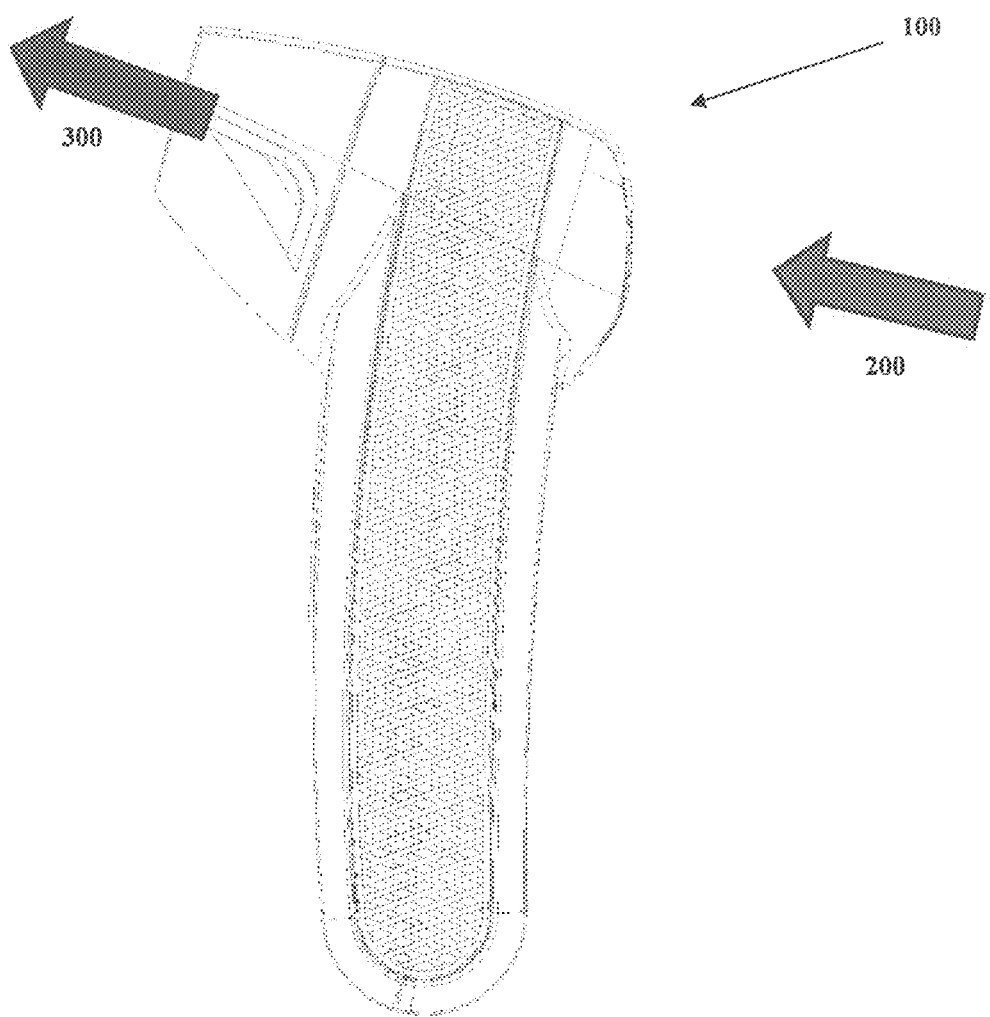
FIG. 7 is a perspective view of the developed safety portable incense heater operation showing air flow direction.

Referring to FIGS. 2, 3 and 7 the Fan 64 mounted on the top inner side of rear housing 20 and in line with the inlet grill 21, the fresh air 200 will be sucked through the inlet grill 21 and it will be drives through the air duct guide 41 which mounted on the other side of the fan 64, silicon rubber rings 35 placed between the fan 64 and the airduct 41 to prevent parts vibration inside the present invention, the air will go around the heater housing 50 and goes through the air holes 13 on the front housing 10 with high speed, a suction force will be generated inside the heating chamber 55, the heating chamber 55 is the place were the users put their incense material, using the physics of suction force which generated by the air traveling inside the present invention, the air will carry the fragrance smoke from inside the heating chamber 55 to the outlet grill 31 spreading the incense fragrance smoke with high speed air 300 outside to the users.

Referring to FIG. 3, the outlet cap 30 comprises of outlet grill 31 were the high-speed fragrance air spread out to the users, right and left curved grooves 32 helps the users for easily grapping the outlet cap and to open it in order to place the incense material in the heating chamber 55, from the other side of the outlet cap 30, mesh metal sheet 38 is mounted on the outlet cap by upper silicon rubber 36 and lower silicon rubber 37, the uses of the mesh metal sheet 38 is to prevent the incense material to fall or moves from inside the heating chamber 55.

Figure 6:
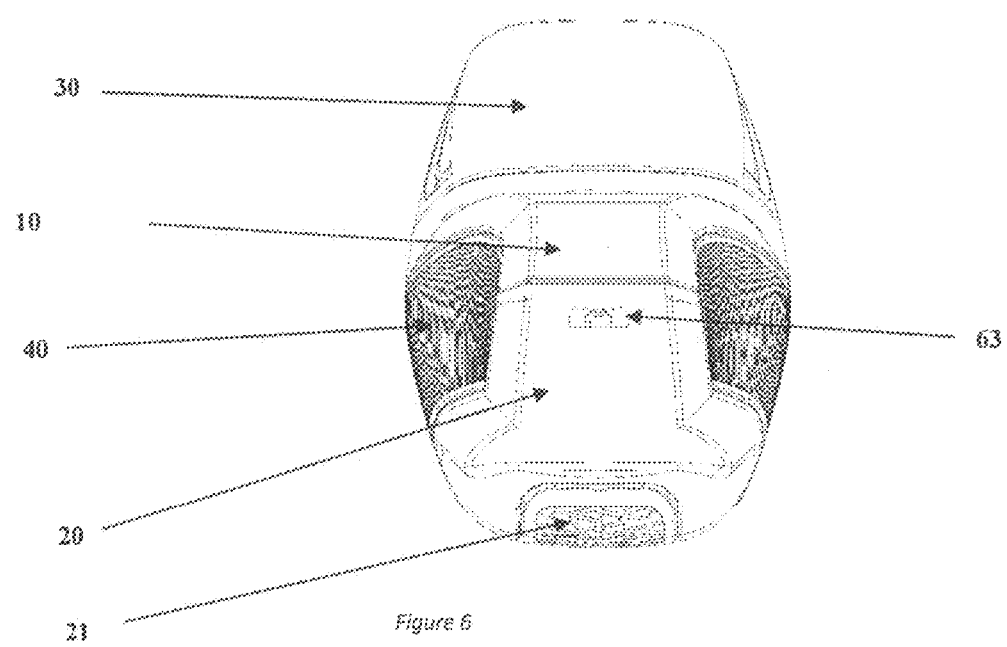
FIG. 6 is a perspective view of the present invention from the bottom side.

Referring to FIGS. 3 and 6 the electronic PCB 60 is placed behind the front housing and its mounted on battery bracket 42, the uses of the battery bracket 42 is to keep the battery 65 in its place, from the other side of the battery 65 a foam sheet 43 is placed between the battery 65 and the rear housing 20 to prevent the battery from shaking, underneath the battery 65 electronic USB-PCB 62 were its used to recharges the battery 65 through the USB port 63.

Figure 4:
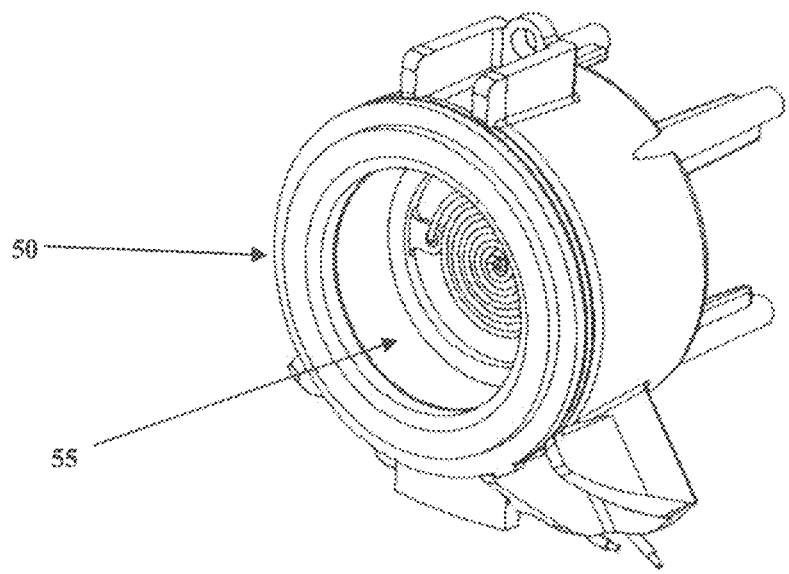
FIG. 4 is a perspective view of the heater housing and Bukhoor chamber.
Figure 5:
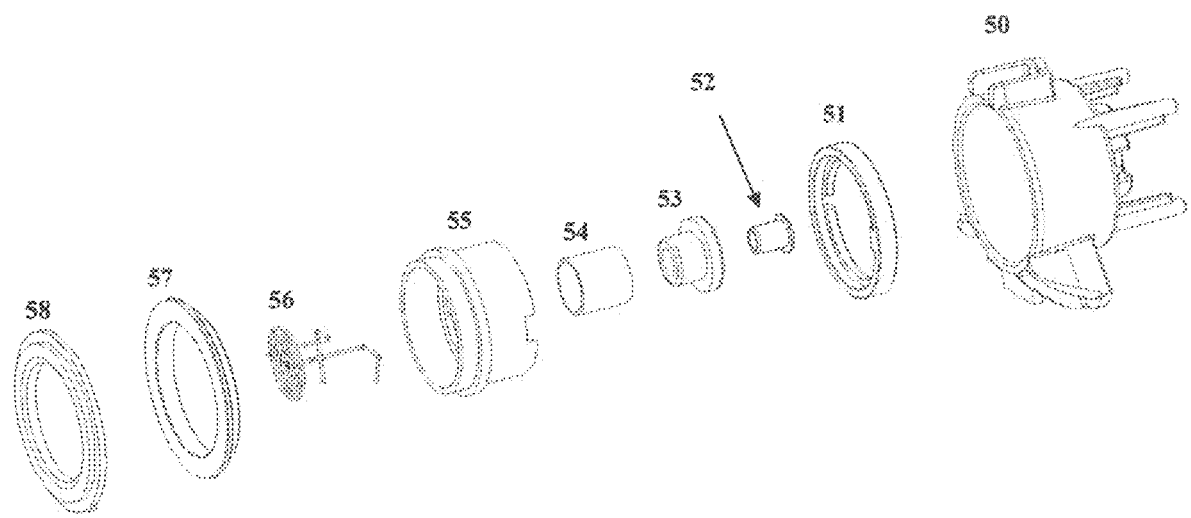
FIG. 5 is a detailed exploded view of the heater housing and Bukhoor chamber.

Referring to FIGS. 3, 4 and 5, the heating housing 50 comprises of inner O-ring 51 which holds the heating chamber 55 inside the heating housing 50, heating coil 56 is placed inside the heating chamber 55, inner ceramic 52, outer ceramic 54 and middle silicon rubber 53 mounted behind the heating coil 56 to secure heating coil 56 wires and to prevent short circuits in the present invention, the outer O-ring 57 and circular housing frame 58 is placed respectively on the other side of the heating housing 50 to secure the heating chamber 55 from shaking while using the present invention by the users, the benefits from inner O-ring 51 and outer O-ring 57 is to prevent heats from spreading to the other parts of the present invention and also to secure the heating chamber in its place inside the heating housing 50.

Referring to FIGS. 3 and 4, heating coil 56, electronic USB-PCB 62, fan 64 and battery 65 are connected to the electronic PCB 60 by soldering pins wires.
Main switch 11 connected to electronic PCB 60 mechanically on the top of trigger button 66 which soldered in the electronic PCB 60.

It is to be understood that the present invention is not limited to the embodiments described above but encompasses any and all embodiments within the scope of the following claims.

The invention claimed is:

1. A developed safety portable incense heater comprising:
   a hollow housing body having a horizontal housing attached to a vertical housing;
   wherein the vertical housing comprising a rear and front vertical housing having a bottom curved end to be mounted with the rear vertical housing and a right and left vertical grill housing attached to both the front and the rear vertical housing;
   wherein the horizontal housing comprises a hinge arm connected from the front end to an outlet cap housing forming a one part and from the rear end to the top surface of the rear vertical housing through a hinge spring mounted inside the hinge arm end to hold the hinge arm while the users opens the hinge arm;
   a fan mounted on the top inner side of the rear vertical housing in the same horizontal axis with an inlet grill attached to the rear vertical housing allowing fresh air to be sucked and derived through an airduct guide mounted on the other side of the fan towards and around a heater housing generating a suction force inside an incense heating chamber mounted inside the heating housing while the air will carry the fragrance smoke from inside the incense heating chamber to the front outlet grill spreading the incense fragrance smoke with high speed air outside to users; and
   silicon rubber rings placed between the fan and the airduct preventing vibration inside the horizontal housing.

2. A developed safety portable incense heater according to claim 1, wherein the outlet cap housing comprises:
   a front outlet grill;
   a right and left curved grooves helping the users for easily opening the outlet cap; and
   a mesh metal sheet mounted on the outlet cap by an upper silicon rubber and a lower silicon rubber preventing the incense material to fall or move from inside the incense heating chamber.

3. A developed safety portable incense heater according to claim 2, wherein the outlet cap having a cone-shaped.

4. A developed safety portable incense burner according to claim 1, wherein the hollow housing body having a reversed L-shaped.

5. A developed safety portable incense burner according to claim 1, wherein the heating housing comprises:
   an inner O-ring holds the incense heating chamber inside the heating housing;
   a heating coil placed inside the heating chamber;
   an inner and outer ceramic with a middle silicon rubber mounted behind the heating coil securing the heating coil wires and preventing short circuits happened; and
   an outer O-ring and a circular housing frame placed respectively on the other side of the heating housing securing the heating chamber from shaking and preventing heats from spreading.

6. A developed safety portable incense heater according to claim 1, further comprising a circuit housing housed inside said vertical housing, wherein the circuit housing comprises:
   a main switch, LED status indicator both housed in the front vertical housing and connected to an electronic PCB behind the front vertical housing and mounted on a battery bracket for keeping a rechargeable battery fixed in its place;
   a foam sheet placed between the rechargeable battery and the rear vertical housing preventing the rechargeable battery from shaking; and
   a USB port underneath the rechargeable battery.

7. A developed safety portable incense heater comprising:
   a hollow housing body comprises a rear and front vertical housing having a bottom curved end to be mounted with the rear vertical housing and a right and left vertical grill housing attached to both the front and the rear vertical housing;
   a hinge arm connected from the front end to a cone outlet cap housing forming a one part and from the rear end to the top surface of the rear vertical housing through a hinge spring mounted inside the hinge arm end to hold the hinge arm while the users opens the hinge arm, wherein the cone outlet cap housing comprises a front outlet grill and a right and left curved grooves helping the users for easily opening the outlet cap;
   a main switch and LED status indicator both housed in the front vertical housing and connected to an electronic PCB behind the front vertical housing and mounted on a battery bracket for keeping a rechargeable battery fixed in its place, a foam sheet placed between the rechargeable battery and the rear vertical housing preventing the rechargeable battery from shaking; and a fan mounted on the top inner side of the rear vertical housing in the same horizontal axis with an inlet grill attached to the rear vertical housing; and an airduct guide mounted on the other side of the fan allowing fresh air to be sucked and derived towards and around a heater housing generating a suction force inside an incense heating chamber mounted inside the heating housing while the air will carry the fragrance smoke from inside the incense heating chamber to the front outlet grill spreading the incense fragrance smoke with high speed air outside to users.

8. A developed safety portable incense burner according to claim 7, further comprising a mesh metal sheet mounted on the outlet cap by an upper silicon rubber and a lower silicon rubber preventing the incense material to fall or move from inside the incense heating chamber.

9. A developed safety portable incense burner according to claim 7, wherein the heating housing comprises:

an inner O-ring holds the incense heating chamber inside the heating housing;

a heating coil placed inside the heating chamber;

an inner and outer ceramic with a middle silicon rubber mounted behind the heating coil securing the heating coil wires and preventing short circuits happened; and an outer O-ring and a circular housing frame placed respectively on the other side of the heating housing securing the heating chamber from shaking and preventing heats from spreading.

10. A developed safety portable incense burner according to claim 7, further comprising a USB port underneath the rechargeable battery.

11. A developed safety portable incense burner according to claim 7, further comprising silicon rubber rings placed between the fan and the airduct preventing vibration inside the horizontal housing.

* * * * *